United States Patent [19]
Johnson

[11] Patent Number: 5,906,025
[45] Date of Patent: May 25, 1999

[54] RING-SHAPED SUCTION HEAD FOR EVACUATING FLUIDS FROM SURGICAL OPERATING ROOM FLOORS

[76] Inventor: Theodore D. Johnson, 2219 Glenmoor Rd., South Clearwater, Fla. 34624

[21] Appl. No.: 08/859,091

[22] Filed: May 20, 1997

[51] Int. Cl.⁶ .................................................. A47L 9/02
[52] U.S. Cl. .......................................... 15/415.1; 604/317
[58] Field of Search .................. 15/322, 339, 415.1, 15/417, 420; 604/313, 317, 902

[56] References Cited

U.S. PATENT DOCUMENTS

| | | |
|---|---|---|
| 2,533,697 | 12/1950 | Stewart . |
| 2,966,694 | 1/1961 | Brown, Jr. . |
| 3,605,171 | 9/1971 | Candor et al. . |
| 3,780,398 | 12/1973 | Candor . |
| 4,041,569 | 8/1977 | Petersen . |
| 4,156,948 | 6/1979 | Chauvier et al. . |
| 4,193,156 | 3/1980 | Chauvier . |
| 4,677,705 | 7/1987 | Schuster . |
| 4,679,590 | 7/1987 | Hergenroeder . |
| 4,729,404 | 3/1988 | Hergenroader . |
| 5,014,389 | 5/1991 | Ogilvie et al. . |
| 5,032,184 | 7/1991 | Ogilvie et al. . |
| 5,549,707 | 8/1996 | Weaver . |

FOREIGN PATENT DOCUMENTS 309158  11/1955  France .

*Primary Examiner*—Terrence R. Till

[57] ABSTRACT

A ring-shaped suction head for containing and aspirating fluids falling to the floor of a surgical operating room has a flow channel recessed in the bottom surface of a ring-shaped body, a suction port communicating with the flow channel and a containment wall extending from the bottom surface to define a fluid containment area within the body. The ring-shaped configuration defines an opening through the body coinciding with the containment area and permitting grasping with the hand for positioning the suction head on the floor of the operating room, particularly under a stream of fluid to contain the fluid within the body.

13 Claims, 2 Drawing Sheets

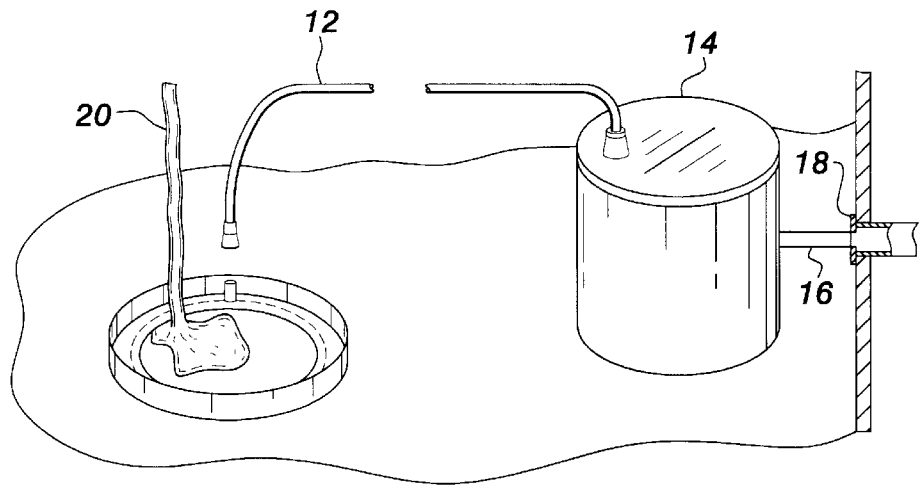
FIG. 1
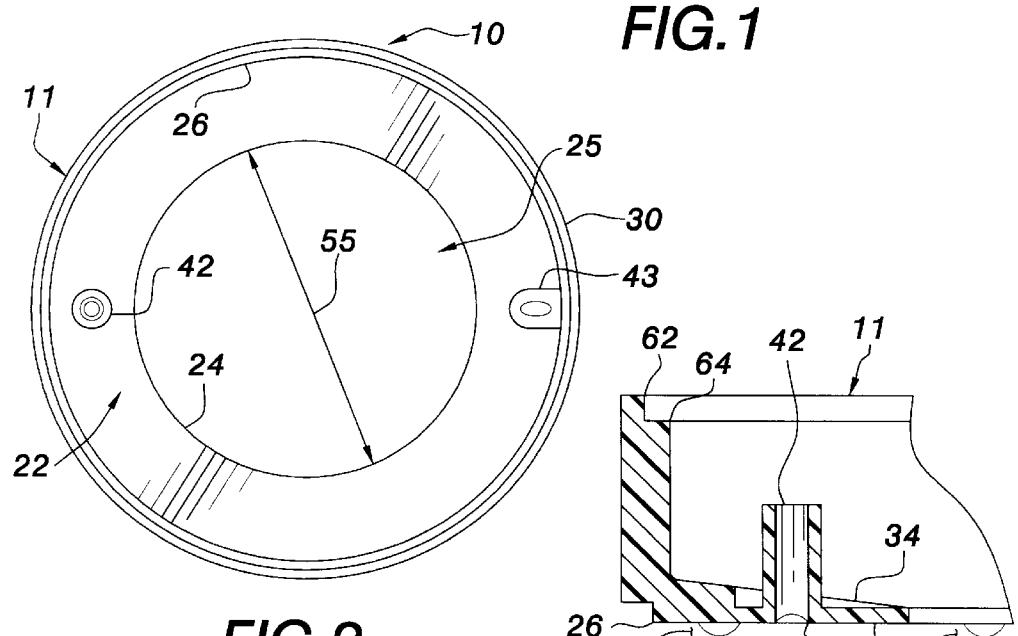
FIG. 2
FIG. 4
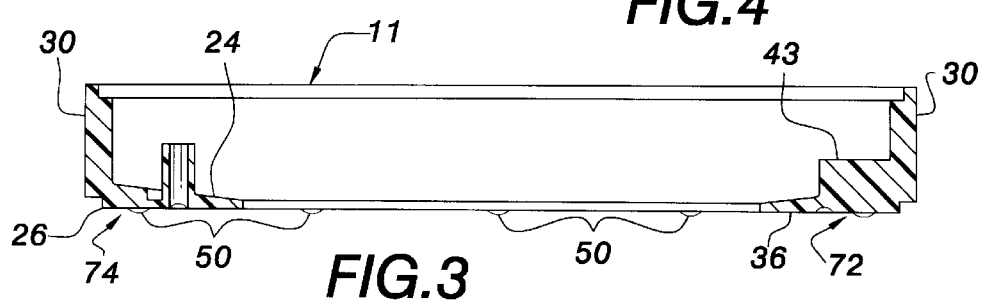
FIG. 3

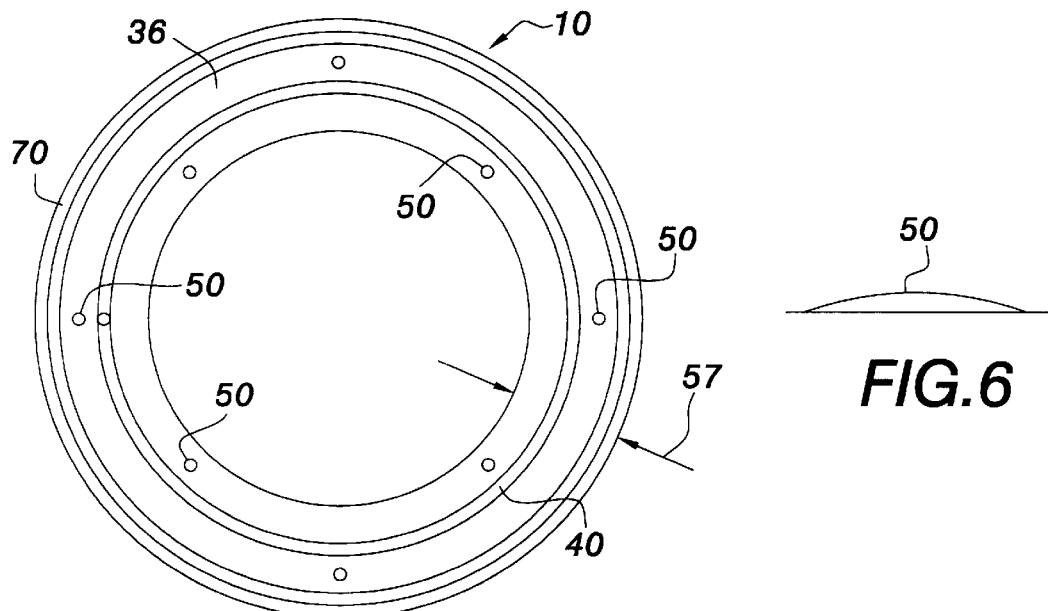
FIG.5
FIG.6
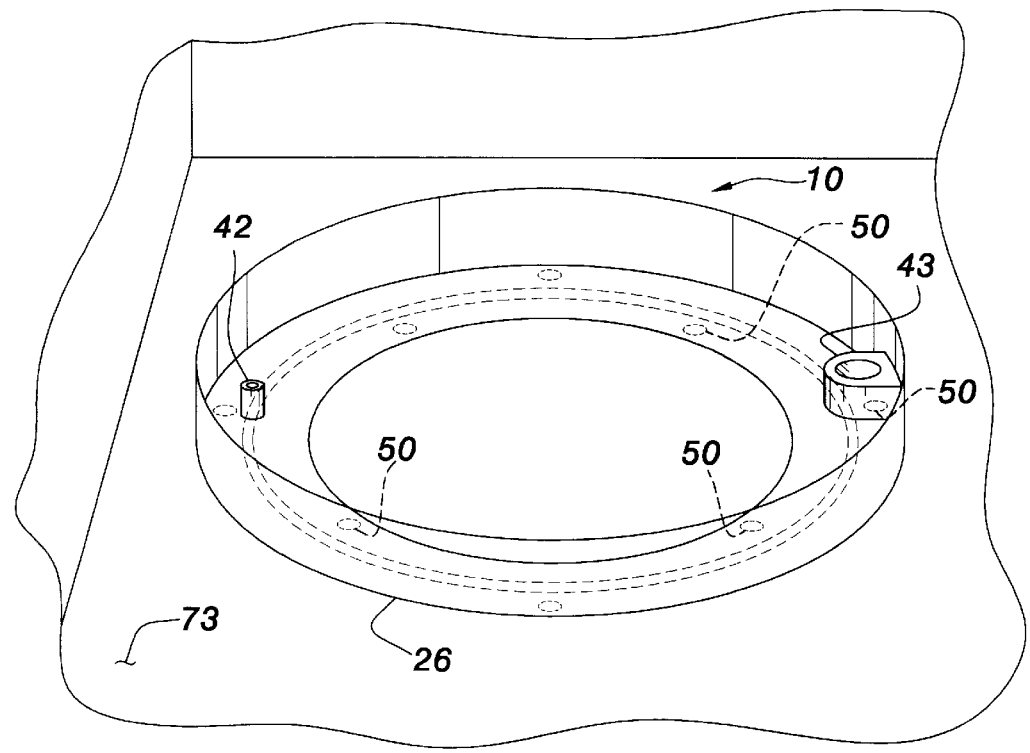
FIG.7

RING-SHAPED SUCTION HEAD FOR EVACUATING FLUIDS FROM SURGICAL OPERATING ROOM FLOORS

BACKGROUND OF THE INVENTION

1. Field of the Invention

The present invention relates to removing fluid that drains or spills onto the floor during a surgical procedure and, more particularly to a ring-shaped suction head for use with suction sources commonly available in a surgical operating room.

2. Discussion of the Prior Art

During the course of surgery, waste fluids of various types find their way onto the floor of the operating room. Specifically, during arthroscopic surgery, sterile fluid (e.g., saline solution) is supplied to the surgical site as a distension medium for the joint. The fluid, if permitted to accumulate and puddle on the floor, presents a safety hazard in that operating room personnel are likely to slip and fall. The possible contamination of the fluid presents an additional hazard. In urological surgery, such fluids may fall to the floor in an intermittent or continuous stream. If such fluids are allowed to collect on the operating room floor, they will puddle, thereby creating a safety hazard and biohazard to the operating room personnel.

A number of approaches have been disclosed in attempts to solve this problem. In particular, U.S. Pat. Nos. 4,679,590 and 4,729,404 to Hergenroeder disclose a rubber mat adapted for placement beneath the surgical site in sealed engagement with the floor. The top surface of the mat is configured as multiple inverted pyramidal elements to collect fluid and direct it to a drain hole on the bottom side of the mat. The bottom side of the mat is provided with flow channels that become sealed to the floor and converge to a common suction port adapted for connection to a source of suction commonly available at a wall-mounted port in surgical operating rooms. Suction delivers the recovered fluid to a canister for collection and disposal.

Although the suction-mat arrangement described in the Hergenroeder patents adequately removes fluid falling onto the mat, it cannot drain fluid that falls to the floor beyond the mat periphery. During arthroscopic surgery, the sterile fluid delivered to the surgical site is often delivered at relatively high pressures, thereby making it difficult for surgical personnel to direct the fluid from the surgical site onto the suction mat. It is also difficult to pick up the mat and place it over a puddle once a vacuum source has been applied since the mat effectively seals itself to the floor.

There are commercially available vacuum cleaners with movable suction heads adapted to draw liquid from floors toward a waste collection chamber. These devices, however, are not suitable for surgical environments for a number of reasons. Since operating room personnel are otherwise occupied during a surgical procedure, the use of a commercial vacuum cleaner would require additional personnel thereby adding to the cost of the surgery. Moreover, commercially available vacuum cleaners have built-in vacuum sources that are extremely noisy thereby rendering communication between the surgeon and the nurses more difficult. It would be far more desirable to use a low-level suction source (e.g., on the order of 300 mm of mercury below atmospheric pressure) such as is commonly available at a wall port in operating rooms; however, suction heads employed with commercial vacuum cleaners are incapable of operating at such low pressure differentials. The stand-alone vacuum cleaner is also not a timely solution since the puddle must be allowed to form before it can be cleaned up. As noted above, the fluids that spill onto the floor during a surgical procedure are likely to be or become contaminated and hence present a biohazard. Commercially available vacuum cleaner heads for liquids are not designed to be disposable after use and, accordingly, would become contaminated and present a health hazard.

Another approach to solution of this problem has been presented in U.S. Pat. Nos. 5,014,389 and 5,032,184 to Ogilvie et al which disclose a suction head for use in removing waste fluids from surgical operating room floors having a planar, low friction bottom surface adapted to readily slide along the floor in response to translational forces applied by surgery personnel using their feet. A plurality of flow channels are recessed in the bottom surface and extend radially from the mouth of a common suction port in the center of the suction head to the periphery of the suction head for connection by flexible tubing to a waste fluid collection canister. The suction head is a thin, solid, one-piece molded plate with radial reinforcing ribs made from plastic. The Ogilvie et al suction head is not particularly useful, however, for cleaning up the steady or intermittent falling stream of fluid which may be encountered in arthroscopic or urological surgery since the radial suction channels connected to the suction inlet are located on the bottom surface and open to atmosphere only at the periphery (i.e., along the outer edge) of the suction head. The suction head cannot catch the falling fluid before it splashes and puddles since the fluid simply strikes the solid or closed upper surface of the suction head from above and splashes outwardly or rolls to the periphery of the suction head. Once a puddle on the operating room floor is established, the Ogilvie et al suction head must be moved in place to remove the fluid thereby permitting the initial formation of a dangerous puddle before the suction head becomes effective. The solid top surface and radial, downward facing flow channels are, thus, not suitable for preventing contamination of the operating room floor by splashing and puddling of falling liquids.

OBJECTS AND SUMMARY OF THE INVENTION

Accordingly, it is a primary object of the present invention to overcome the above mentioned disadvantages of the prior art by providing a suction head for efficiently removing fluids from surgical room floors while preventing accumulation and puddling from continuous or intermittent falling streams of waste fluid.

A further object of the present invention is to provide a ring-shaped suction head that is easily grasped by hand and positioned on the floor under a falling stream of fluid.

A further object of the present invention is to provide a ring-shaped suction head which will mitigate splashing from a falling stream of fluid.

A further object of the present invention is to provide a suction head for use in conjunction with available suction sources in surgical operating rooms, the suction head being sufficiently inexpensive to be disposable after a single surgical procedure and relatively quiet in operation.

In accordance with the present invention, a suction head for use in removing fluids from surgical operating room floors is formed of a ring-shaped body defining an opening therethrough and having a bottom surface and a wall defining a fluid containment area coinciding with the opening through the ring-shaped body, a flow channel in the bottom surface and a suction port communicating with the flow channel.

In use, the suction port is coupled by flexible tubing to a waste fluid collection container or canister which can be connected by a hose to a wall-mounted suction source providing a negative, low pressure on the order of 300 mm of mercury below atmospheric pressure. Aspirated waste fluids are drawn into the flow channel and removed through the flexible tubing. The wall contains fluid as the fluid falls into the opening or containment area and accumulates. The top of the wall may include a stepped interior surface for containing splashes and funneling fluid down into the opening or interior aperture. The body can have an upper surface preferably sloped down toward the interior aperture to enhance the funneling of the fluids. The bottom surface has an irregular surface, such as rounded protrusions or feet to prevent the suction head from sealing to the floor. The suction head may easily be manually grasped by the wall and placed anywhere on the floor for aspiration of waste fluids.

In the preferred embodiment, the suction head is a thin, one-piece, molded ring, preferably of brightly colored, transparent, resilient plastic material, and is sufficiently inexpensive to be discarded after each surgical procedure.

The foregoing and additional objects, features and advantages of the invention will become apparent to those of skill in the art from the following detailed description of a preferred embodiment, taken with the accompanying drawings wherein like reference numerals in the various drawings identify like components.

BRIEF DESCRIPTION OF THE DRAWINGS

FIG. 1 is a perspective of a waste fluid aspiration system incorporating the ring-shaped suction head of the present invention positioned on the operating room floor.

FIG. 2 is a top view of the suction head of the present invention.

FIG. 3 is a cross-sectional view of the suction head of the present invention.

FIG. 4 is an enlarged view in section of one side of the suction head of the present invention.

FIG. 5 is a bottom view of the suction head of the present invention.

FIG. 6 is a side view of a support foot on the bottom surface of the suction head of the present invention.

FIG. 7 is a perspective of the suction head of the present invention positioned on the operating room floor

DESCRIPTION OF THE PREFERRED EMBODIMENT

Referring specifically to FIG. 1 of the accompanying drawings, a system for aspiration of waste fluids according to the present invention includes a ring-shaped suction head 10 connected by a flexible hose 12 to a waste liquid vacuum collection canister 14. Another hose 16 is connected between the canister 14 and a wall suction port 18 of the type commonly found in surgical operating rooms for supplying low-level suction (on the order of 300 mm of mercury below atmospheric pressure). Hoses 12 and 16 communicate with the interior of the canister 14 through respective fittings such that suction from the wall port 18 is applied through the canister 14 to suction head 10, and aspirated fluid, upon reaching the canister, is sufficiently heavy (in relation to the low suction) to drop into the canister 14 for collection and eventual disposal.

Suction head 10 and hose 12 are preferably disposable after a single surgical procedure. If canister 14 is provided with a permanent collection hose, disposable hose 12 may be inserted between the permanent hose and the suction head 10. The hose 12 between canister 14 and suction head 10 is very flexible and of sufficient length to permit easy placement of suction head 10 on the floor of the operating room at any appropriate location. The suction head 10 is preferably grasped by hand for positioning on the floor in a manner which will permit containment and aspiration or evacuation of a steady or intermittent falling stream of waste fluid 20 to prevent puddling since any waste fluid is aspirated and transported away by vacuum before a puddle can expand and contaminate the operating room floor.

Suction head 10 is preferably molded of a polymer as a single, disposable, lightweight ring-shaped body. In a preferred embodiment, a polymeric material known as C-FLEX thermoplastic elastomer is used. The basic formula of the C-FLEX material is described in U.S. Pat. Nos. 4,386,179 and 4,613,640, the disclosures of which are incorporated herein by reference. Briefly, the base component of the C-FLEX material is a styrene-ethylene/butylene-styrene block copolymer (SEBS). The C-FLEX material is well suited to making suction heads in bright colors for easy visibility, and in a preferred embodiment, a fluorescent green-yellow is used. The SEBS material is readily rendered in a transparent finished product which operating room staff can see through during use. By "transparent" is meant light transmissive and sufficiently optically non-distorting to permit operating room staff to see fluid through the suction head.

The suction head 10 of FIG. 1 is illustrated in greater detail in FIGS. 2, 3, 4, 5, 6 and 7, to which specific reference is now made. As shown in FIGS. 2, 3 and 4, the suction head 10 includes a ring-shaped body 11 formed of an annular flange 22 having an inner edge 24 defining an interior aperture 25 and stepped outer edge 26 from which extends a perpendicular, annular containment wall 30. The flange 22 has a top surface 34 sloping down from the outer flange edge 26 to the inner flange edge 24 and has a bottom surface 36.

As shown in FIG. 5, an annular groove or flow channel 40 is concentrically recessed within the bottom surface 36 of flange 22, and a vacuum connection tube or suction port 42 is situated on the top surface 34 of the flange 22 and communicates with the flow channel 40 on the bottom surface 36 of the flange. A mold sink or sprue 43 protrudes from flange 22 at a position diametrically across from suction port 42. The bottom surface 36 has an irregular contour to create spaces between the floor and the flange to provide communication with the flow channel 40. In a preferred embodiment, the irregular contour is formed by a plurality of rounded protrusions, bumps or feet 50 radially arrayed on the bottom surface 36 of the flange. FIG. 6 illustrates an enlarged side view of one of the feet 50. The feet 50 raise the bottom surface 36 of the flange 30 above the floor to create a space defining an interior suction area 72 adjacent inner edge 24 and an exterior, peripheral suction area 74 adjacent outer edge 26.

In a preferred embodiment, the outer diameter of the suction head 10 is approximately eight inches, the inner diameter 55 of the opening or interior aperture 25 is approximately 5 inches, the flange radial width 57 is approximately 1.5 inches, the feet are substantially semi-spherical, 0.005 inches in height and 0.062 inches in diameter. As illustrated in FIG. 5, there are eight feet, four feet being arrayed radially at equal spacing (i.e., 90°) along a first constant radius outside the flow channel 40 on the flange bottom surface 36 and four feet being radially arrayed at equal spacing (i.e., 90°) at a second constant radius inside the flow channel 40. The flow channel 40 is roughly centered in the flange bottom surface 36 and has an outside diameter of approximately 6.5 inches. The radial width of the flow channel is approximately 0.25 inches and its depth is 0.0625 inches. The flow channel 40 is preferably radiused; however, the flow channel can have any cross-section of sufficient area to permit flow of entrained fluids. The flange 40 is approximately 0.2 inches thick at the outer edge 26 and is radiused in a smooth transition from vertical at the containment wall 30. The flange upper surface 34 slopes down to a thickness of approximately 0.063 inches at the flange inner edge 24. The height 60 of containment wall 30 is approximately 1 inch. The interior suction area 72 has a height of about 0.005 inches and a length (inner circumference) of about sixteen inches. For these dimensions, the inner suction area is about 0.08 square inches. The peripheral suction area 74 has the same height, but with a length (outer circumference) of about 23.8 inches to define an area of approximately 0.12 inches. The total suction area is, thus, about 0.2 inches and varies linearly with the height of feet 50 to vary suction area, face velocity and flow rate of the suction head 10. The top edge 62 of wall 30 is thinner than the remainder of the wall. A shoulder or step 64 defines the upward most end of the thicker portion of the wall 30, and the inner edge of step 64 defines a transition to a thinner upper wall section. The stepped interior of wall 30 and the sloped upper surface 34 of the flange function together as a funnel, draining fluid toward the interior aperture 25.

In use, flexible vacuum hose 12 is connected to the vacuum connection tube 42. The ring-shaped suction head 10 is placed on the operating room floor as illustrated in FIG. 1. The feet 50 serve to prevent the suction head from engaging with the floor in a sealing relation due to the vacuum present in annular groove 40 by providing a clearance or space between the bottom surface of the flange 36 and the floor thereby allowing a suction to be present around the outer perimeter 70 of the suction head 10 as well as along the inner edge of the flange 24. The suction head 10 can be used to dispose of materials which fall within the opening of the ring-shaped body 11 defining interior aperture 25 as well as spills which lie outside of the suction head. Any fluid spilled on the operating room floor in close proximity to the suction head is aspirated into the space between the floor and the bottom surface 36 of the body 11 and into the space beneath the flow channel 40. The fluid is then drawn toward the suction port 42 and out through the flexible hose 12 and into canister 14. Suction head 10 may be readily positioned beneath a continuous or intermittent stream 20 of fluid during a surgical procedure. If the flow of fluid is too great for instantaneous aspiration using the vacuum supplied by flexible line 12, the fluid will simply accumulate inside of the containment area defined by the floor 73 and containment wall 30 while the vacuum system removes it safely to the canister 14. Greater containment capacity can be provided by simply enlarging the height 60 of the wall 30 or the diameters of the flange 22 and wall 30. The containment feature significantly reduces the likelihood of fluid creating a large puddle on the floor. The containment wall stepped edge 64 also acts as a splash guard to reduce spreading of splashed droplets of waste fluid.

The suction head of the present invention is subject to many variations and modifications. For example, a spiral flow channel or a series of concentric flow channels could be used instead of the single annular groove 40. A reservoir can be incorporated within the containment area thereby eliminating the use of an additional vacuum connector. The suction head may be made of any durable, sterilizable material. The suction head need not be circular but can have any ring-shaped configuration, such as being oval, hexagonal, or rectangular, as long as a groove or recess can be formed in the bottom surface and the body encircles or surrounds a containment area. Any shape having a useful large and wide opening or containment area will suffice. The wall 30 forming a fluid containment barrier can extend substantially transversely from the flange at any portion thereof; however, the body 11 need not be made of a separate flange and wall in that the body 11 can have a shape defining a bottom surface and a wall such that the ring-shaped body defines an opening therethrough and the wall defines a fluid containment area coinciding with the opening.

Inasmuch as the present invention is subject to various modifications and changes in detail, the above description of a preferred embodiment is intended to be exemplary only and not limiting.

What is claimed is:

1. A suction head for evacuating fluids from a surgical operating room floor comprising a ring-shaped body defining an opening therethrough and having a bottom surface with inner and outer edges and a wall defining a fluid containment area coinciding with said opening within said ring-shaped body, a downwardly facing flow channel recessed in said bottom surface of said ring-shaped body between said inner and outer edges of said bottom surface; and a suction port communicating with said flow channel whereby fluid within said containment area can be evacuated through said flow channel and said suction port when said suction port is connected with a source of suction.

2. A suction head as recited in claim 1 wherein said bottom surface of said ring-shaped body has an irregular contour to create spaces between the floor and portions of said bottom surface to provide communication between said containment area and said flow channel.

3. A suction head as recited in claim 2 wherein said irregular contour is formed by a plurality of rounded protrusions extending from a substantially planar surface.

4. A suction head as recited in claim 2 wherein said flow channel extends entirely around said ring-shaped body.

5. A suction head for evacuating fluids from a surgical operating room floor comprising a ring-shaped body defining an opening therethrough and having a bottom surface adapted to engage the floor and a wall defining a fluid containment area coinciding with said opening within said ring-shaped body;

a flow channel recessed in said bottom surface of said ring-shaped body; and a suction port communicating with said flow channel whereby fluid within said containment area can be evacuated through said flow channel and said suction port when said suction port is connected with a source of suction;

wherein said ring-shaped body is integrally formed of one piece of transparent polymer material.

6. A suction head as recited in claim 5 wherein said ring-shaped body has a circular configuration defining an inner edge coinciding with said opening and an outer peripheral edge and said bottom surface of ring-shaped body is spaced from the floor by said irregular contour adjacent said outer peripheral edge to provide communication between the periphery of said ring-shaped body and said flow channel.

7. A suction head for use with a vacuum source in a surgical operating room to evacuate fluids comprising:

a circuital, horizontal flange having a bottom surface, a top surface and a continuous inside edge defining an interior aperture;

a flow channel recessed in said bottom surface of said flange;

a suction port passing through said flange from said flow channel to said upper surface of said flange; and a circuital containment wall extending substantially transversely from said top surface of said flange whereby said flange and said containment wall define containment area for fluids to be evacuated.

8. The suction head as recited in claim 7 wherein said flange has an outer edge and said containment wall extends upwardly from said outer edge.

9. A suction head as recited in claim 8 wherein said horizontal flange has an outside edge and said top surface slopes downwardly from said outside edge to said inside edge.

10. A suction head as recited in claim 9 wherein said suction head is molded of polymer material.

11. A suction head as recited in claim 10 wherein said polymer material is a styrene-ethylene/butylene-styrene block copolymer.

12. A suction head as recited in claim 9 wherein said polymer material is transparent.

13. A suction head as recited in claim 9 wherein said containment wall includes a thicker section, a thinner section and a stepped transition between said thicker section and said thinner section.

* * * * *